(12) United States Patent
Melville

(10) Patent No.: US 8,437,587 B2
(45) Date of Patent: May 7, 2013

(54) ACTUATING AN OPTICAL FIBER WITH A PIEZOELECTRIC ACTUATOR AND DETECTING VOLTAGES GENERATED BY THE PIEZOELECTRIC ACTUATOR

(75) Inventor: Charles David Melville, Issaquah, WA (US)

(73) Assignee: University of Washington, Seattle, WA (US)

( * ) Notice: Subject to any disclaimer, the term of this patent is extended or adjusted under 35 U.S.C. 154(b) by 22 days.

(21) Appl. No.: 11/881,278

(22) Filed: Jul. 25, 2007

(65) Prior Publication Data

US 2009/0026888 A1    Jan. 29, 2009

(51) Int. Cl.
*A61B 1/04* (2006.01)
*A61B 1/00* (2006.01)
*A61B 6/00* (2006.01)

(52) U.S. Cl.
USPC .............. 385/15; 600/118; 600/476; 385/901

(58) Field of Classification Search .................. 385/901; 600/118, 476
See application file for complete search history.

(56) References Cited

U.S. PATENT DOCUMENTS

| | | |
|---|---|---|
| 4,234,788 A | 11/1980 | Palmer et al. |
| 4,264,208 A | 4/1981 | Haberl et al. |
| 4,710,619 A | 12/1987 | Haberl |
| 4,743,283 A | 5/1988 | Borsuk |
| 4,768,513 A | 9/1988 | Suzuki |
| 4,770,185 A | 9/1988 | Silverstein et al. |
| 4,782,228 A | 11/1988 | Westell |
| 4,821,117 A | 4/1989 | Sekiguchi et al. |
| 4,831,370 A | 5/1989 | Smoot |
| 4,872,458 A | 10/1989 | Kanehira et al. |
| 4,963,018 A | 10/1990 | West |
| 5,081,350 A | 1/1992 | Iwasaki et al. |
| 5,172,685 A | 12/1992 | Nudelman |
| 5,178,130 A | 1/1993 | Kaiya |
| 5,315,383 A | 5/1994 | Yabe et al. |
| 5,360,968 A | 11/1994 | Scott |
| 5,454,807 A | 10/1995 | Lennox et al. |
| 5,455,669 A | 10/1995 | Wetteborn |
| 5,459,570 A | 10/1995 | Swanson et al. |
| 5,557,444 A | 9/1996 | Melville et al. |

(Continued)

FOREIGN PATENT DOCUMENTS

| | | |
|---|---|---|
| EP | 1360927 | 11/2003 |
| EP | 1864606 | 12/2007 |

(Continued)

OTHER PUBLICATIONS

"Electronic linearization of piezoelectric actuators and noise budget in scanning probe microscopy," by Aloisi et al, Review of Scientific Instruments, vol. 77, No. 7, Jul. 5, 2006, pp. 073701-1 through 073701-6.*

(Continued)

*Primary Examiner* — Ryan Lepisto
*Assistant Examiner* — Robert Tavlykaev
(74) *Attorney, Agent, or Firm* — Blakely Sokoloff Taylor & Zafman LLP

(57) ABSTRACT

A method of one aspect may include actuating a cantilevered optical fiber by mechanically deforming a piezoelectric actuator. An electrical signal generated as a result of mechanical deformation of the piezoelectric actuator may also be detected.

17 Claims, 8 Drawing Sheets

U.S. PATENT DOCUMENTS

| | | | |
|---|---|---|---|
| 5,596,339 A | 1/1997 | Furness, III et al. |
| 5,627,922 A | 5/1997 | Kopelman et al. |
| 5,694,237 A | 12/1997 | Melville |
| 5,695,491 A | 12/1997 | Silverstein |
| 5,701,132 A | 12/1997 | Kollin et al. |
| 5,751,465 A | 5/1998 | Melville et al. |
| 5,784,098 A | 7/1998 | Shoji et al. |
| 5,822,073 A | 10/1998 | Yee et al. |
| 5,822,486 A | 10/1998 | Svetkoff et al. |
| 5,887,009 A | 3/1999 | Mandella et al. |
| 5,894,122 A | 4/1999 | Tomita |
| 5,903,397 A | 5/1999 | Melville et al. |
| 5,913,591 A | 6/1999 | Melville |
| 5,939,709 A | 8/1999 | Ghislain et al. |
| 5,969,871 A | 10/1999 | Tidwell et al. |
| 5,982,528 A | 11/1999 | Melville |
| 5,982,555 A | 11/1999 | Melville et al. |
| 5,991,048 A | 11/1999 | Karlson et al. |
| 5,995,264 A | 11/1999 | Melville |
| 6,046,720 A | 4/2000 | Melville et al. |
| 6,049,407 A | 4/2000 | Melville |
| 6,061,163 A | 5/2000 | Melville |
| 6,069,698 A | 5/2000 | Ozawa et al. |
| 6,069,725 A | 5/2000 | Melville |
| 6,097,353 A | 8/2000 | Melville et al. |
| 6,154,321 A | 11/2000 | Melville et al. |
| 6,157,352 A | 12/2000 | Kollin et al. |
| 6,166,841 A | 12/2000 | Melville |
| 6,191,761 B1 | 2/2001 | Melville et al. |
| 6,204,832 B1 | 3/2001 | Melville et al. |
| 6,220,711 B1 | 4/2001 | Melville et al. |
| 6,243,186 B1 | 6/2001 | Melville et al. |
| 6,257,727 B1 | 7/2001 | Melville |
| 6,263,234 B1 | 7/2001 | Engelhardt et al. |
| 6,281,862 B1 | 8/2001 | Tidwell et al. |
| 6,285,505 B1 | 9/2001 | Melville et al. |
| 6,288,816 B1 | 9/2001 | Melville et al. |
| 6,294,775 B1 | 9/2001 | Seibel et al. |
| 6,317,548 B1 | 11/2001 | Rockwell et al. |
| 6,369,953 B2 | 4/2002 | Melville et al. |
| 6,388,641 B2 | 5/2002 | Tidwell et al. |
| 6,411,838 B1 | 6/2002 | Nordstrom et al. |
| 6,441,359 B1 | 8/2002 | Cozier et al. |
| 6,492,962 B2 | 12/2002 | Melville et al. |
| 6,535,183 B2 | 3/2003 | Melville et al. |
| 6,538,625 B2 | 3/2003 | Tidwell et al. |
| 6,560,028 B2 | 5/2003 | Melville et al. |
| 6,563,105 B2 | 5/2003 | Seibel et al. |
| 6,581,445 B1 | 6/2003 | Weiss |
| 6,627,903 B1 | 9/2003 | Hirayanagi |
| 6,700,552 B2 | 3/2004 | Kollin et al. |
| 6,734,835 B2 | 5/2004 | Tidwell et al. |
| 6,747,753 B1 | 6/2004 | Yamamoto |
| 6,817,973 B2 * | 11/2004 | Merril et al. ............... 600/118 |
| 6,845,190 B1 | 1/2005 | Smithwick et al. |
| 6,850,673 B2 | 2/2005 | Johnston, II et al. |
| 6,856,712 B2 | 2/2005 | Fauver et al. |
| 6,867,753 B2 | 3/2005 | Chinthammit et al. |
| 6,959,130 B2 | 10/2005 | Fauver et al. |
| 6,975,898 B2 | 12/2005 | Seibel |
| 6,977,631 B2 | 12/2005 | Melville et al. |
| 7,068,878 B2 | 6/2006 | Crossman-Bosworth et al. |
| 7,123,790 B2 | 10/2006 | Rosman et al. |
| 7,159,782 B2 | 1/2007 | Johnston et al. |
| 7,184,150 B2 | 2/2007 | Qualing et al. |
| 7,189,961 B2 | 3/2007 | Johnston et al. |
| 7,230,583 B2 | 6/2007 | Tidwell et al. |
| 7,252,236 B2 | 8/2007 | Johnston et al. |
| 7,277,819 B2 | 10/2007 | Marcus et al. |
| 7,346,417 B2 * | 3/2008 | Luth et al. ............... 700/117 |
| 2001/0055462 A1 | 12/2001 | Seibel |
| 2002/0010384 A1 | 1/2002 | Shahidi et al. |
| 2002/0062061 A1 | 5/2002 | Kaneko et al. |
| 2002/0064341 A1 | 5/2002 | Fauver et al. |
| 2002/0080359 A1 | 6/2002 | Denk et al. |
| 2002/0093467 A1 | 7/2002 | Tidwell et al. |
| 2002/0093563 A1 | 7/2002 | Cline et al. |
| 2002/0097498 A1 | 7/2002 | Melville et al. |
| 2002/0139920 A1 | 10/2002 | Seibel et al. |
| 2003/0004412 A1 | 1/2003 | Izatt et al. |
| 2003/0010825 A1 | 1/2003 | Schmidt et al. |
| 2003/0010826 A1 | 1/2003 | Dvorkis et al. |
| 2003/0016187 A1 | 1/2003 | Melville et al. |
| 2003/0048540 A1 | 3/2003 | Xie et al. |
| 2003/0142042 A1 | 7/2003 | Tidwell et al. |
| 2003/0169966 A1 | 9/2003 | Tokizaki |
| 2003/0202361 A1 | 10/2003 | Johnston et al. |
| 2004/0061072 A1 | 4/2004 | Gu et al. |
| 2004/0122328 A1 | 6/2004 | Wang et al. |
| 2004/0153030 A1 | 8/2004 | Novak |
| 2004/0196213 A1 | 10/2004 | Tidwell et al. |
| 2004/0254474 A1 | 12/2004 | Seibel et al. |
| 2005/0013526 A1 * | 1/2005 | Lee et al. ............... 385/13 |
| 2005/0020926 A1 | 1/2005 | Wiklof et al. |
| 2005/0025368 A1 | 2/2005 | Glukhovsky |
| 2005/0085708 A1 | 4/2005 | Fauver et al. |
| 2005/0085721 A1 | 4/2005 | Fauver et al. |
| 2005/0174610 A1 | 8/2005 | Fukawa |
| 2005/0182295 A1 | 8/2005 | Soper et al. |
| 2005/0238277 A1 | 10/2005 | Wang et al. |
| 2006/0072189 A1 | 4/2006 | DiMarzio et al. |
| 2006/0072843 A1 | 4/2006 | Johnston |
| 2006/0072874 A1 | 4/2006 | Johnston |
| 2006/0077121 A1 | 4/2006 | Melville et al. |
| 2006/0138238 A1 * | 6/2006 | Johnston et al. ......... 235/462.32 |
| 2006/0149134 A1 | 7/2006 | Soper et al. |
| 2006/0186325 A1 | 8/2006 | Johnston et al. |
| 2006/0195014 A1 | 8/2006 | Seibel et al. |
| 2006/0226231 A1 | 10/2006 | Johnston et al. |
| 2006/0287647 A1 | 12/2006 | Torchia et al. |
| 2007/0081168 A1 | 4/2007 | Johnston et al. |
| 2007/0091426 A1 | 4/2007 | Johnston et al. |
| 2007/0096594 A1 * | 5/2007 | Maruyama et al. ........... 310/317 |
| 2007/0129601 A1 | 6/2007 | Johnston et al. |
| 2007/0135693 A1 | 6/2007 | Melman et al. |
| 2007/0156021 A1 | 7/2007 | Morse et al. |
| 2007/0273930 A1 | 11/2007 | Berier et al. |
| 2007/0278311 A1 * | 12/2007 | Partyka ............... 235/462.36 |
| 2008/0021490 A1 * | 1/2008 | Briggs et al. ............... 606/181 |
| 2008/0144998 A1 | 6/2008 | Melville et al. |
| 2008/0161648 A1 | 7/2008 | Karasawa |

FOREIGN PATENT DOCUMENTS

| | | |
|---|---|---|
| GB | 2378259 | 2/2003 |
| JP | 08211313 | 8/1996 |
| JP | 2003-083749 | 3/2003 |
| WO | WO-9300551 | 1/1993 |
| WO | WO-01/74266 | 10/2001 |
| WO | WO-2004/040267 | 5/2004 |
| WO | WO-2006004743 | 1/2006 |
| WO | WO-2006041452 | 4/2006 |
| WO | WO-2006071216 | 7/2006 |
| WO | WO2006096155 | 9/2006 |
| WO | WO-2006/106853 | 10/2006 |
| WO | WO-2006104489 | 10/2006 |
| WO | WO-2006124800 | 11/2006 |
| WO | WO-2007018494 | 2/2007 |
| WO | WO-2007/023940 | 3/2007 |
| WO | WO-2008/033168 | 3/2008 |

OTHER PUBLICATIONS

"PCT/US2007/009598 International Search Report", (Jan. 3, 2008), 3 pages.

"PCT/US2007/017439 International Search Report", (Apr. 17, 2008), 5 pages.

Barhoum, Erek S., et al., "Optical modeling of an ultrathin scanning fiber endoscope, a preliminary study of confocal versus non-confocal detection", *Optics Express*, vol. 13, No. 19, (Sep. 8, 2005), pp. 7548-7562.

Brown, Christopher, et al., "A Novel Design for a Scanning Fiberoptic Endoscope", *Human Interface Technology Laboratory, University of Washington*, Seattle, WA 98195, Presented at SPIE's Regional Meeting on Optoelectronics, Photonics, and Imaging, (Nov. 1-2, 1999), 1 page.

Brown, Christopher M., et al., "Mechanical Design and Analysis for a Scanning Fiber Endoscope", *Proceedings of 2001 ASME Int'l Mechanical Engineering Congress and Exposition*, BED—vol. 51, (Nov. 11-16, 2001), 165-166.

Chen, Tailian, et al., "Experiment of Coalescence of Dual Bubbles on Micro Heaters", *Department of Mechanical Engineering, University of Florida*, Gainesville, FL 32611-6300. USA., Printed from the Internet Aug. 13, 2006, 1-10.

Fauver, Mark, et al., "Microfabrication of fiber optic scanners", (2002) *In Proceedings of of optical Scanning II, SPIE 4773*, pp. 102-110., 9 pages.

Johnston, Richard S., et al., "Scanning fiber endoscope prototype performance", *Optical Fibers and Sensors for Medical Applications II, Proc. SPIE*, vol. 4616, (Oct. 13, 2004), 173-179.

Seibel, Eric J., et al., "A full-color scanning fiber endoscope", *Optical Fibers and Sensors for Medical Diagnosis and Treatment Applications. Ed. I Gannot. Proc. SPIE* vol. 6083, (2006), 9-16.

Seibel, Eric J., et al., "Microfabricated optical fiber with microlens that produces large field-of-view, video rate, optical beam scanning for microendoscopy applications", *Optical Fibers and Sensors for Medical Applications III, Proceedings of SPIE vol. 4957*, (2003), 46-55.

Seibel, Eric J., et al., "Modeling optical fiber dynamics for increased efficiencies in scanning fiber applications", *Optical Fibers and Sensors for Medical Applications V, proceedings of SPIE vol. 5691*, (2005), 42-53.

Seibel, Eric J., et al., "P-37: Optical fiber scanning as a microdisplay source for a wearable low vision aid", *Society for Information Display SID 2002*, Boston, MA, (May 19-24, 2002), 1-4.

Seibel, Eric J., et al., "Prototype scanning fiber endoscope", *Optial Fibers and Sensors for Medical Applications II, Proc. of SPIE*, vol. 4616, (2002), 1-7.

Seibel, Eric J., et al., "Single fiber flexible endocope: general design for small size, high resoljution, and wide field of view", *Human Interface Technology Laboratory, College of Engineering, University of Washington*, Seattle, WA, Proceedings of the SPIE, Biomonitoring and Endoscopy Technologies 4158, (2001), 11 pages.

Seibel, Eric J., et al., "Ultrathin laser scanning bronchoscope and guidance system for the peripheral lung", *11th World Conference on Lung Cancer*, (2005), p. 178.

Seibel, Eric J., et al., "Unique Features of Optical Scanning, Single Fiber Endoscopy", *Lasers in Surgery and Medicine 30*, (2002), 177-183.

Seibel, Eric, et al., "Unique Features of Scanning Fiber Optical Endopscopy", *2000 Annual Fall Meeting Abstracts T4.57*, (2000), 1.

Smithwick, Quinn Y., et al., "54.3: Modeling and Control of the Resonant Fiber Scanner for Laser Scanning Display or Acquisition", *Department of Aeronautics and Astronautics, University of Washington*, Seattle, WA *SID 03 Digest*, (2003), 1455-1457.

Smithwick, Quinn Y., et al., "A Nonlinear State-Space Model of a Resonating Single Fiber Scanner for Tracking Control: Theory and Experiment", *Transactions fo the ASME*, vol. 126, (Mar. 2004), 88-101

Smithwick, Quinn Y., et al., "Control Aspects of the Single Fiber Scanning Endoscope", (2001) *i SPIE Optical Fibers and Sensors for Medical Applications*, 4253, 176-188., 15 pages.

Smithwick, Quinn Y., et al., "Depth Enhancement using a Scanning Fiber Optical Endoscope", *Department of Aeronautics, Human Interface Technology Laboratory, University of Washington*, Seattle, Washington, Optical Biopsy IV, Proc. SPIE 4613, (2002), 12 pages.

Tuttle, Brandon W., et al., "Delivery of therapeutic laser light using a singlemode silica fiber for a scanning fiber endoscope system", *Optical Fibers and Sensors for Medical Diagnostics and Treatment Applications VI, Proc. of SPIE vol. 6083*,, (2006) 608307-1 to608307-12.

Wang, Wei-Chih, et al., "Development of an Optical Waveguide Cantilever Scanner", *Opto-Ireland 2002: Optics and Photonics Technologies and Applications, Proceedings of SPIE vol. 4876* (2003), 72-83.

Wang, Wei-Chih, et al., "Micromachined opital waveguide cantilever as a resonant optical scanner", *Department of Mechanical Engineering, University of Washington*, Seattle, WA 98195, *Sensors and Actuators A 102*, (2002), 165-175.

Aloisi et al., "Electronic Linearization of Piezoelectric Actuators and Noise Budget in Scanning Probe Microscopy", Review of Scientific Instruments, vol. 77, No. 7, Jul. 5, 2006, pp. 073701-1 through 073701-6.

"PCT International Preliminary Report on Patentability", PCT/US2007/017439, mailed Feb. 4, 2010, pp. 1-9.

\* cited by examiner

ACTUATING AN OPTICAL FIBER WITH A PIEZOELECTRIC ACTUATOR AND DETECTING VOLTAGES GENERATED BY THE PIEZOELECTRIC ACTUATOR

BACKGROUND

1. Field

Embodiments of the invention relate to piezoelectric actuators. In particular, embodiments of the invention relate to both actuating cantilevered optical fibers with piezoelectric actuators and detecting voltages generated by the piezoelectric actuators.

2. Background Information

Scanning fiber devices may be used for image acquisition and/or display. The scanning fiber devices often include a cantilevered optical fiber that may be vibrated, moved, or otherwise actuated in one or two dimensions.

A common way of actuating the cantilevered optical fiber is with a piezoelectric actuator. Voltages or other electrical actuation signals may be applied to the piezoelectric actuator. The applied electrical signals may mechanically deform or change the shape of a piezoelectric material of the actuator. Such mechanical deformation may actuate the cantilevered optical fiber. However, actuating the cantilevered optical fiber with the piezoelectric actuator so that it moves exactly as intended sometimes tends to be challenging.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details are set forth. However, it is understood that embodiments of the invention may be practiced without these specific details. In other instances, well-known circuits, structures and techniques have not been shown in detail in order not to obscure the understanding of this description.

In addition to actuating a cantilevered optical fiber with a piezoelectric actuator, in embodiments of the invention, voltages or other electrical signals generated by the piezoelectric actuator due to mechanical deformation may be detected. In one aspect, such electrical signals may be used to estimate the position and/or movement of the piezoelectric actuator and/or the cantilevered optical fiber. In another aspect, the estimated position and/or movement may be used as a sort of feedback to improve the actuation of the cantilevered optical fiber so that it moves more as intended.

Figure 1:
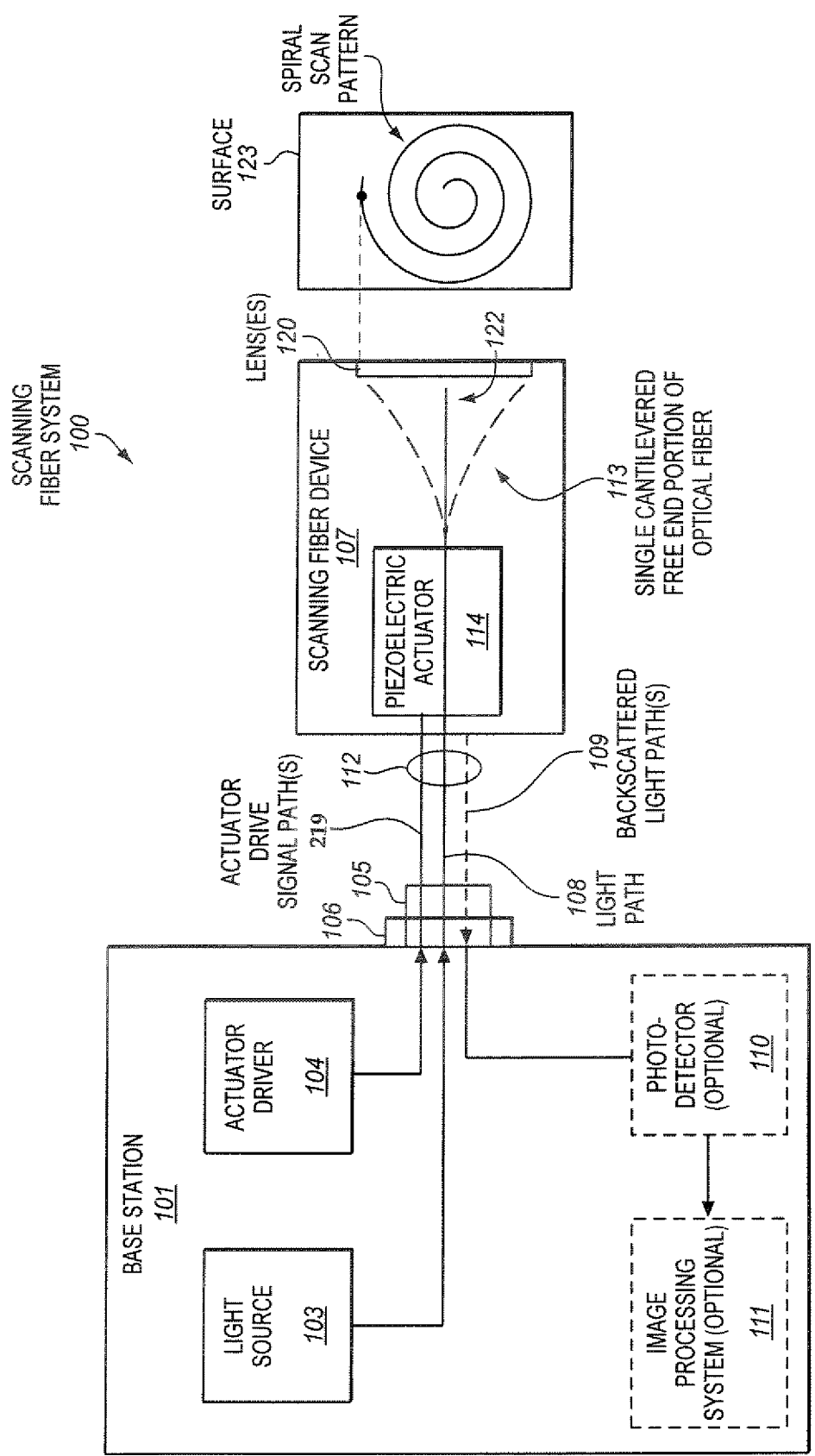
FIG. 1 is a block diagram of an example scanning fiber system, according to embodiments of the invention.

FIG. 1 is a block diagram of an example scanning fiber system 100, according to embodiments of the invention. The scanning fiber system has a two-part form factor that includes a base station 101 and a scanning fiber device 107, although such a two-part form factor is not required. The scanning fiber device is electrically and optically coupled with the base station through one or more cables 112. In particular, the scanning fiber device includes a connector 105 to connect or mate with a corresponding connector interface 106 of the base station.

The base station includes a light source 103 to provide light to the scanning fiber device through a light path 108. Examples of suitable light sources include, but are not limited to, lasers, laser diodes, vertical cavity surface-emitting lasers (VCSELs), light-emitting diodes (LEDs), and combinations thereof. In various example embodiments of the invention, the light source may include a red light source, a blue light source, a green light source, a red-green-blue (RGB) light source, a white light source, an infrared light source, an ultraviolet light source, a high intensity therapeutic laser light source, or a combination thereof. Depending on the particular implementation, the light source may emit a continuous stream of light, modulated light, or a stream of light pulses.

The base station also includes an actuator driver 104 to provide voltages or other electrical signals, referred to herein as actuator drive signals, to the scanning fiber device. The actuator drive signals may be provided through one or more actuator drive signal paths 219. The actuator driver may be implemented in hardware (for example a circuit), software (for example a routine or program), or a combination of hardware and software. As one example, in one or more embodiments of the invention, the actuator driver may include one or more lookup tables or other data structures stored in a memory that may provide actuator drive signal values. The actuator drive signal values may potentially be adjusted based on calibration, such as, for example, as described in U.S. Patent Application 20060072843, entitled "REMAPPING METHODS TO REDUCE DISTORTIONS IN IMAGES", by Richard S. Johnston. As another example, the actuator driver may include a computer, processor, application specific integrated circuit (ASIC), or other circuit to generate the actuator drive signal values in real time. The values may be digital and may be provided to a digital-to-analog converter of the actuator driver. One or more amplifiers of the actuator driver may amplify the analog versions of the actuator drive signals. These are just a few illustrative examples of suitable actuator drivers.

The scanning fiber device 107 includes a single cantilevered free end portion of an optical fiber 113 and a piezoelectric actuator 114. Examples of suitable types of piezoelectric actuators include, but are not limited to, piezoelectric tubes, piezoelectric beams, piezoelectric cantilevers, piezoelectric disks, other piezoelectric materials, devices, or structures capable of actuating the cantilevered optical fiber, and combinations thereof. The piezoelectric actuator includes a piezoelectric material but may also optionally include one or more non-piezoelectric materials, for example a metal.

The piezoelectric actuator may receive the actuator drive signals. The piezoelectric actuator may move, vibrate, or otherwise actuate the cantilevered optical fiber based on, and responsive to, the received actuator drive signals. A characteristic of piezoelectric materials is that they may mechanically deform or change shape in response to an applied electric field or signal. Such mechanical deformation or change of shape may actuate the cantilevered optical fiber. In embodiments of the invention, the actuator drive signals may be operable to cause the piezoelectric actuator to move the cantilevered optical fiber in a two-dimensional scan pattern. Examples of suitable two-dimensional scan patterns include, but are not limited to, spiral scan patterns, propeller scan patterns, Lissajous scan patterns, circular scan patterns, oval scan patterns, raster scan patterns, and the like.

The cantilevered optical fiber may receive the light from the light source. The light may be emitted from a distal end or tip 122 of the cantilevered optical fiber, while the optical fiber is scanned. The emitted light may be passed through one or more lenses 120 to generate a focused beam or illumination spot that may be moved across a surface 123 in the scan. In the illustration, a spiral scan pattern is shown and a dot shows a position of the illumination spot at a particular point in time.

The scanning fiber system may be used to construct an image. Constructing the image may include displaying or forming an image on the surface and/or acquiring an image of the surface. In displaying the image on the surface, the light emitted from the end of the optical fiber may be modulated during the scan depending on position and passed through the lens system in order to form a desired image on the surface. In acquiring the image of the surface, the scanning fiber device may scan the illumination spot through the lens system and over the surface in the scan. Backscattered light from the surface may be captured at different points in time during the scan and used to construct the image.

In the case of an image acquisition device, different ways of collecting the backscattered light are possible. One or more optical fibers, or other backscattered light paths 109, may optionally be included to collect and convey backscattered light back to one or more optional photodetectors 110 of the base station. Alternatively, the scanning fiber device may optionally include photodetectors proximate a distal tip thereof. As shown, the base station may include an optional image processing system 111 to generate images based on light detected by the photodetectors. A display may be included in the base station or may be externally connected to the base station.

In various embodiments of the invention, the scanning fiber system may take the form of a scanning fiber endoscope, scanning fiber boroscope, scanning fiber microscope, other type of scanning fiber scope, scanning fiber bar code reader, scanning fiber image display device, or other scanning fiber image acquisition and/or display device known in the art. As is known, endoscopes represent instruments or devices to be inserted into a patient to look inside a body cavity, lumen, or otherwise look inside the patient. Examples of suitable types of endoscopes include, but are not limited to, bronchoscopes, colonoscopes, gastroscopes, duodenoscopes, sigmoidoscopes, thorascopes, ureteroscopes, sinuscopes, boroscopes, and thorascopes, to name just a few examples.

A simplified base station has been shown and described in order to avoid obscuring the description. It is to be appreciated that the base station may include other components. Other representative components that may be included in the base station include, but are not limited to, a power source, a user interface, a memory, and the like. Furthermore, the base station may include supporting components like clocks, amplifiers, digital-to-analog converters, analog-to-digital converters, and the like.

Figure 2:
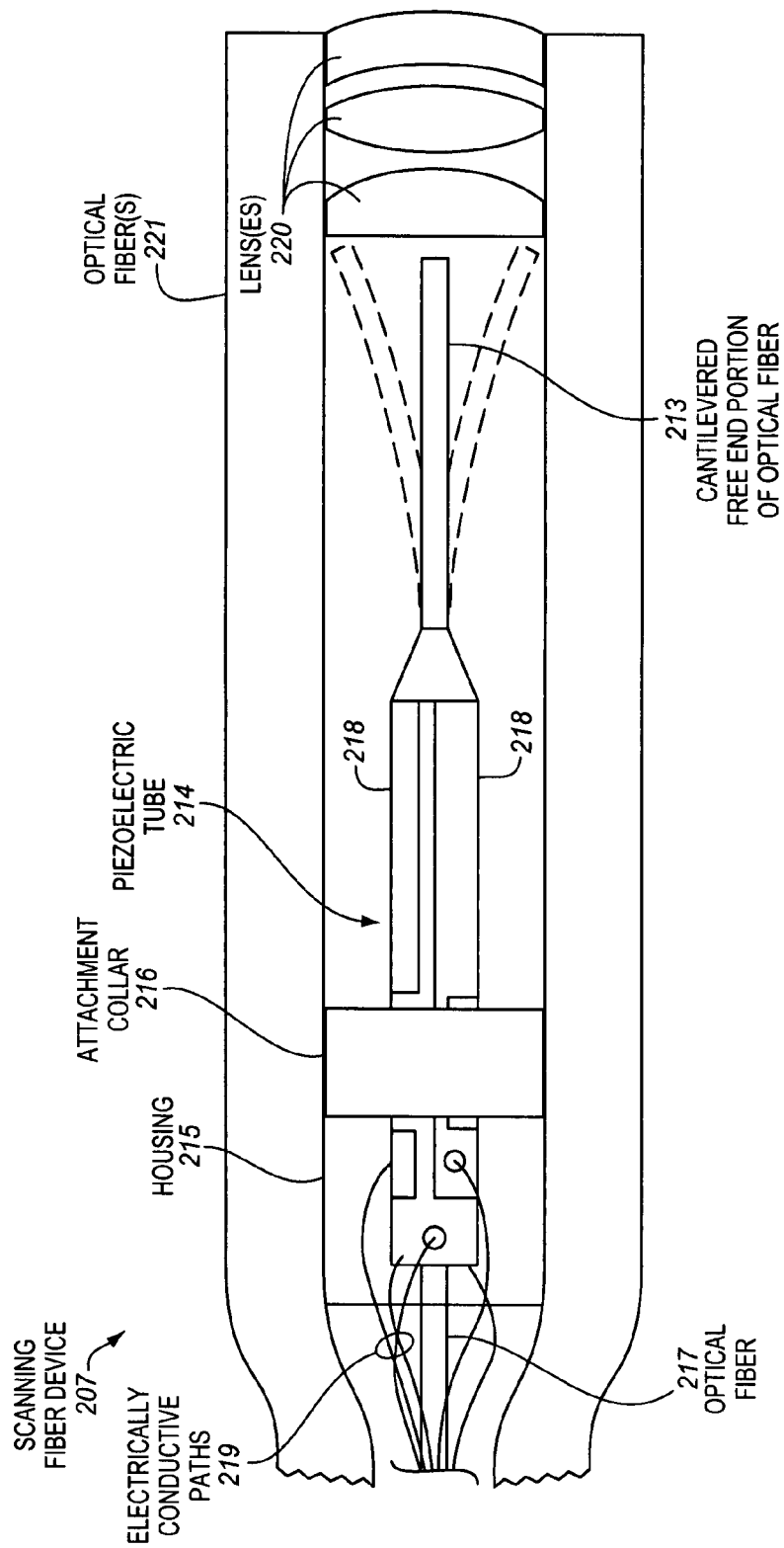
FIG. 2 is a cross-sectional side view of a particular example of a scanning fiber device, according to embodiments of the invention.

FIG. 2 is a cross-sectional side view of a particular example of a scanning fiber device 207, according to embodiments of the invention. This particular scanning fiber device is well suited for use as an endoscope or other relatively small device, although in other implementations the design and operation may vary considerably. Accordingly, it is to be appreciated that this particular scanning fiber device is merely illustrative.

The scanning fiber device includes a housing 215. In one or more embodiments, the housing may be relatively small and hermetically sealed. For example, the housing may be generally tubular, have a diameter that is about 5 millimeters (mm) or less, and have a length that is about 20 mm or less. The housing typically includes one or more lenses 220. Examples of suitable lenses include those manufactured by Pentax Corporation, although other lenses may optionally be used.

As shown, one or more optical fibers 221 may optionally be included around the outside of the housing to collect and convey backscattered light from an illumination spot back to one or more photodetectors, for example located in a base station. Alternatively, one or more photodetectors may be included at or near a distal tip of the scanning fiber device, or omitted entirely.

A piezoelectric tube 214, representing one possible type of piezoelectric actuator, is included in the housing. In one or more embodiments of the invention, the piezoelectric tube may include a PZT 5A material, although this is not required. Suitable piezoelectric tubes are commercially available from several sources including, but not limited to: Morgan Technical Ceramics Sales, of Fairfield, N.J.; Sensor Technology Ltd., of Collingwood, Ontario, Canada; and PI (Physik Instrumente) L.P., of Auburn, Mass. The piezoelectric tube may be inserted through a tightly fitting generally cylindrical opening of the attachment collar. The attachment collar may be used to attach the piezoelectric tube to the housing. Other configurations for the piezoelectric tube and housing are also possible.

A portion of an optical fiber 217 is inserted through a generally cylindrical opening in the piezoelectric tube. A cantilevered free end portion 213 of the optical fiber extends beyond an end of the piezoelectric tube within the housing, and may be attached to the end of the piezoelectric tube, for example with an adhesive. Other configurations of the piezoelectric tube and cantilevered optical fiber are also possible. The cantilevered optical fiber is flexible and may be actuated by the piezoelectric tube.

The piezoelectric tube has electrodes 218 thereon. Wires or other electrically conductive paths 219 are electrically coupled with the electrodes to convey actuator drive signals to the electrodes. As shown, in one example embodiment of the invention, the piezoelectric tube may have four, quadrant metal electrodes on an outer surface thereof. Four electrically conductive paths may respectively be soldered to, or otherwise electrically coupled with, the four electrodes. In one or more embodiments, an optional ground electrode may be included on an inside surface of the piezoelectric tube.

Responsive to receiving the actuator drive signals, the electrodes may apply electric fields to the piezoelectric tube. The electric fields may cause the piezoelectric tube to mechanically deform or change shape. The mechanical deformation may be used to actuate the optical fiber. The four quadrant electrodes, or even only two orthogonal electrodes, may be capable of moving the cantilevered optical fiber in a two-dimensional scan. By way of example, in order to move the cantilevered optical fiber in a spiral scan, same frequency, increasing amplitude, out-of-phase sinusoidal drive signals may be applied to each of the four electrodes.

Now, actuating the cantilevered optical fiber with such a piezoelectric actuator so that it moves exactly as intended sometimes tends to be challenging. For one thing, the piezoelectric actuator and/or the cantilevered optical fiber may not respond exactly as intended to a given set of actuator drive signals. Additionally, the response of the piezoelectric actuator and/or the cantilevered optical fiber to the actuator drive signals may potentially change over time, with changing environmental conditions, or otherwise. As a result, the actual movement and/or position of the piezoelectric actuator and/or the cantilevered optical fiber may deviate from what is expected or intended.

Piezoelectric materials are also capable of generating voltages or other electrical signals in response to mechanical deformation, change of shape, or other mechanical stresses. In embodiments of the invention, voltages or other electrical signals generated by the piezoelectric actuator due to mechanical deformation as a result of motion associated with the actuation of the optical fiber may be detected in real time. In one aspect, such electrical signals may be used to estimate the position and/or movement of the piezoelectric actuator and/or the cantilevered optical fiber. In another aspect, the estimated position and/or movement may be used as a sort of feedback to improve the actuation of the cantilevered optical fiber so that it moves more as intended.

Figure 3:
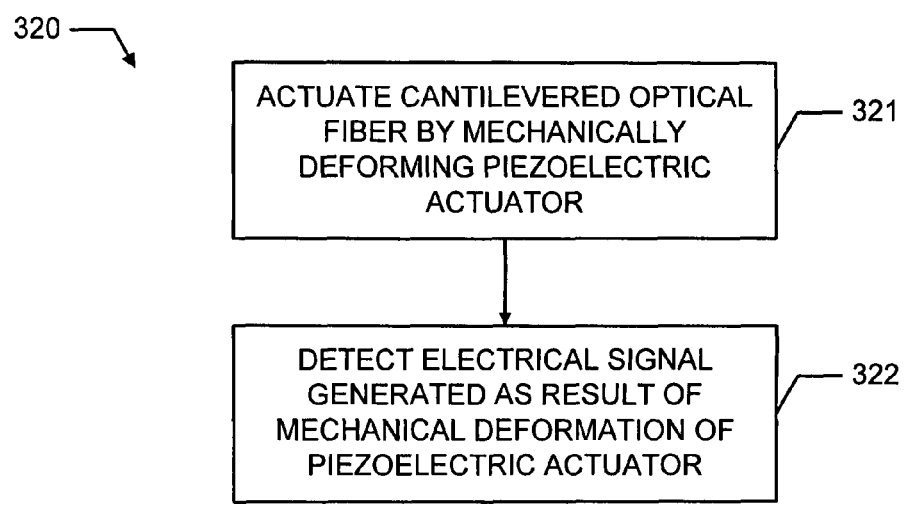
FIG. 3 is a block flow diagram of a method of actuating a cantilevered optical fiber with a piezoelectric actuator and detecting electrical signals generated by the piezoelectric actuator, according to embodiments of the invention.

FIG. 3 is a block flow diagram of a method 320 of actuating a cantilevered optical fiber with a piezoelectric actuator and detecting voltages or other electrical signals generated by the piezoelectric actuator, according to embodiments of the invention.

Initially, a cantilevered optical fiber may be actuated by mechanically deforming a piezoelectric actuator, at block 321. As previously described, this may include applying electrical signals, referred to herein as actuator drive signals, to the piezoelectric actuator. The piezoelectric actuator may be mechanically deformed responsive to the applied actuator drive signals. The cantilevered optical fiber may be actuated due to the mechanical deformation of the piezoelectric actuator. In one or more embodiments of the invention, actuating the cantilevered optical fiber may include vibrating the cantilevered optical fiber at or near, for example within a Q-factor of, a resonant frequency.

Then, voltages or other electrical signals generated as a result of a mechanical deformation of the piezoelectric actuator may be detected, at block 322. As a result of current or previous actuation of the cantilevered optical fiber, the piezoelectric actuator may experience mechanical deformation, such as, for example, deflection of a piezoelectric tube as it traces a spiral scan pattern. The mechanical deformation may cause the piezoelectric actuator to generate voltages or other electrical signals. These electrical signals may be conveyed back to a base station and detected, for example with a voltage detector.

Figure 4:
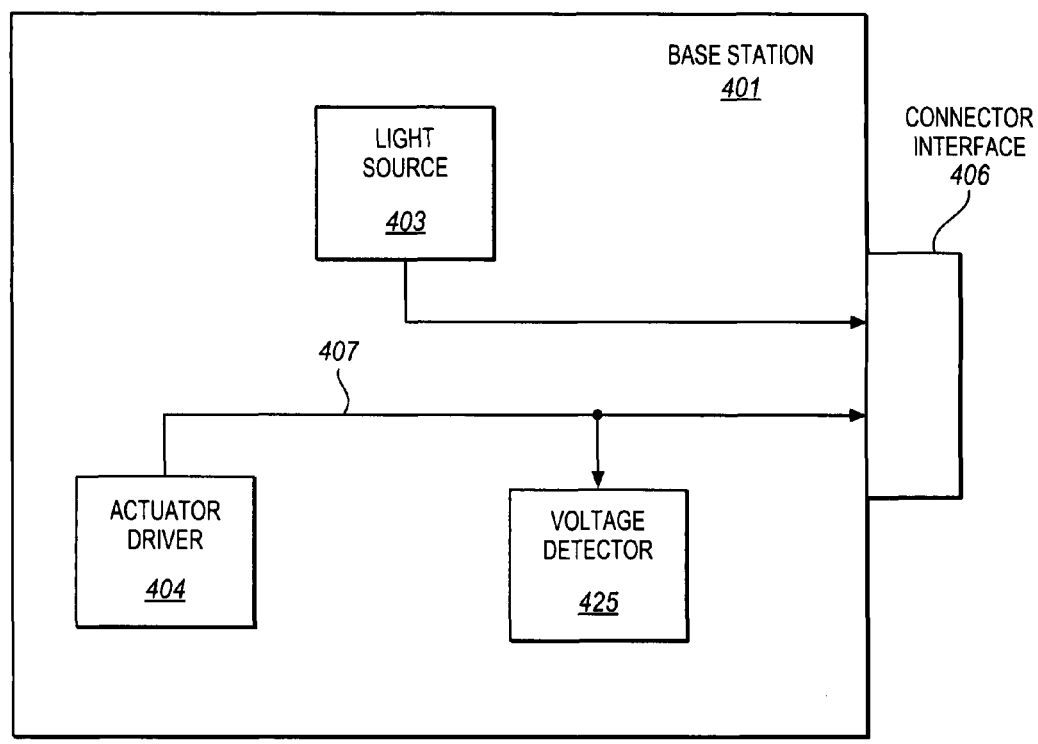
FIG. 4 is a block diagram of a base station, according to embodiments of the invention.

FIG. 4 is a block diagram of a base station 401, according to embodiments of the invention. The base station and its components may optionally have some or all of the characteristics of the correspondingly named components of FIG. 1. To avoid obscuring the description, the discussion below will focus primarily on the different or additional characteristics.

The base station includes a connector interface 406 to allow a scanning fiber device to be connected. A light source 403 of the base station is optically coupled with the connector interface. The light source may provide light to the scanning fiber device through the connector interface. The base station also includes an actuator driver 404. The actuator driver may provide actuator drive signals to a piezoelectric actuator of the scanning fiber device through the connector interface.

The base station also includes at least one voltage detector 425. The voltage detector may detect a voltage, for example a voltage generated due to mechanical deformation of the piezoelectric actuator of the scanning fiber device, which may be returned to the base station through the connector interface. By way of example, in the case of a piezoelectric tube such as that shown in FIG. 2, the voltage detector may be configured to detect a voltage ranging from a few volts to tens of volts (e.g., about 30 volts). However, other ranges may apply for other sizes and types of piezoelectric actuators.

In the illustrated embodiment, the voltage detector is optionally electrically coupled with at least one actuator drive signal path 407 from the actuator driver to the piezoelectric actuator. Alternatively, at least one dedicated voltage detection path may optionally be included from the voltage detector to the piezoelectric actuator. Either the same electrodes used to drive the piezoelectric tube may be used or additional dedicated voltage detection electrodes may be included on the piezoelectric actuator.

In one or more embodiments of the invention, the voltage detector may be at least switchably electrically coupled with a plurality of paths to the piezoelectric actuator. In one or more embodiments of the invention, the voltage detector may be at least switchably electrically coupled with paths leading to a plurality of different sides of the piezoelectric actuator, such as all four sides (top, bottom, right, and left), or two orthogonal sides (e.g., a vertical side and a horizontal side). Detecting voltages associated with at least two orthogonal sides may offer the potential advantage of providing information about position and/or movement in two dimensions. In one or more embodiments of the invention, a dedicated voltage detector may be included in the base station for each electrode for which voltages are to be detected. Alternatively, switching may be used to switchably couple alternate electrodes with a common voltage detector.

The terms "coupled" and "connected," along with their derivatives, are used herein. These terms are not intended as synonyms for each other. Rather, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other physically, electrically, or optically.

In one or more embodiments of the invention, the actuator driver may be capable of being electrically decoupled from the piezoelectric actuator, while the voltage detector detects a voltage generated by the piezoelectric actuator. Decoupling the actuator driver from the piezoelectric actuator may help to prevent, or at least reduce, modification of the voltages or other electrical signals generated by the piezoelectric actuator due to mechanical deformation. Decoupling the actuator driver from the piezoelectric actuator may also help to reduce leaking or dissipation of such voltages or other electrical signals generated by the piezoelectric actuator back to the actuator driver.

Figure 5:
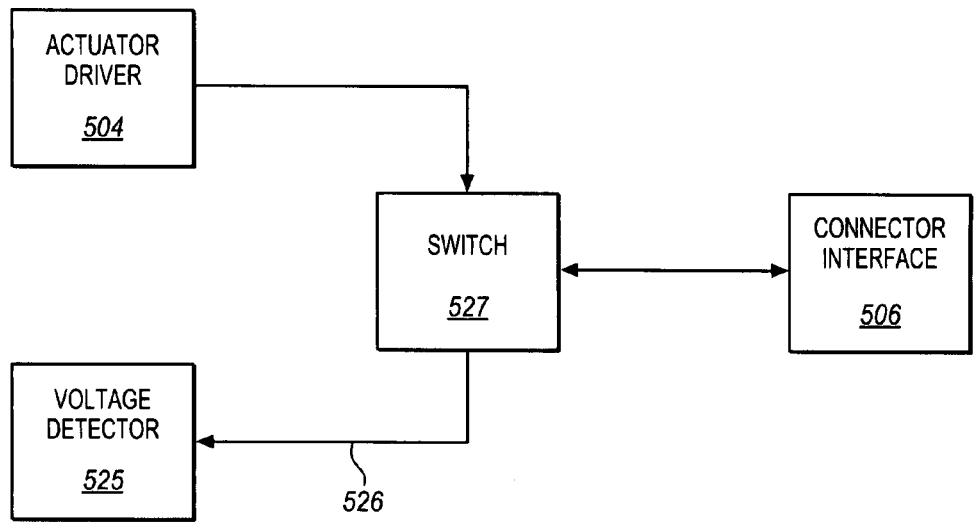
FIG. 5 is a block diagram of a first example configuration for electrically decoupling an actuator driver from a connector interface, according to embodiments of the invention.

FIG. 5 is a block diagram of a first example configuration for electrically decoupling an actuator driver 504 from a connector interface 506, according to embodiments of the invention. In this first approach, a switch 527 is electrically coupled between the actuator driver and the connector interface, and electrically coupled between a voltage detector 525 and the connector interface. Examples of suitable switches include, but are not limited to, discrete component switches, integrated circuit switches, and combinations thereof. As shown, an output of the actuator driver is electrically coupled with the switch. An input of the voltage detector is electrically coupled with the switch. The switch is electrically coupled with the connector interface. The switch is operable to switchably electrically couple or not couple the actuator driver with the connector interface. The switch is also operable to switchably electrically couple or not couple the voltage detector with the connector interface. By way of example, a controller may be electrically coupled with the switch and the switch may be controlled to switch responsive to control signals from the controller. Either, but not both, of the actuator driver, or the voltage detector, may be electrically coupled with the connector interface at one time. In this way, the voltage detector may detect voltages generated by the piezoelectric actuator and returned through the connector interface while the actuator driver is decoupled from the connector interface and therefore also decoupled from the piezoelectric actuator.

Figure 6:
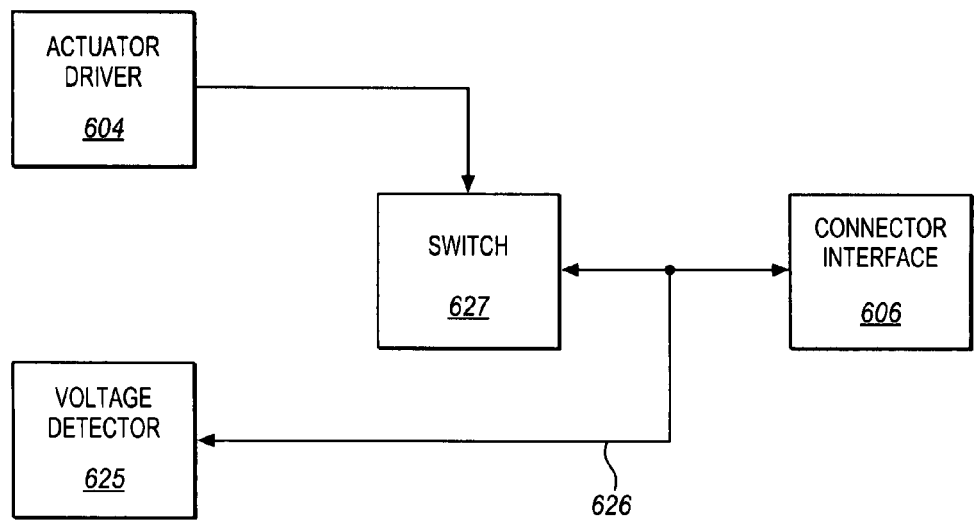
FIG. 6 is a block diagram of a second example configuration for electrically decoupling an actuator driver from a connector interface, according to embodiments of the invention.

Other configurations are also possible. FIG. 6 is a block diagram of a second example configuration for electrically decoupling an actuator driver 604 from a connector interface 606, according to embodiments of the invention. This second approach is similar to the previously described first approach, except that a voltage detector 625 is fixedly (not switchably) electrically coupled with the connector interface. Only the actuator driver is switchably electrically coupled with the connector interface through a switch 627. The voltage detector may detect voltages when the actuator driver is electrically coupled with the connector interface, as well as when the actuator driver is electrically decoupled from the connector interface. The voltages detected when the actuator driver is electrically decoupled from the connector interface may be used, whereas the voltages detected when the actuator driver is electrically coupled with the connector interface may potentially be discarded or ignored.

In one or more embodiments of the invention, a line 526 between the voltage detector 525 and the switch 527 of FIG. 5 may have a high impedance. Likewise, in one or more embodiments of the invention, a line 626 between the voltage detector 625 and the connector interface 606 of FIG. 6 may have a high impedance. The high impedance may provide resistance to the flow of current, which may help to allow a voltage generated by the piezoelectric actuator to be detected without draining away too rapidly. By way of example, the high impedance line may have an impedance of at least one mega ohm. In one aspect, a high impedance amplifier may be included to provide the high impedance.

In one or more embodiments, the detected voltages or other electrical signals may be used to estimate the position and/or movement of the piezoelectric actuator and/or the cantilevered optical fiber. The magnitude of the voltage or other electrical signal is generally directly related to the amount of mechanical deformation of the piezoelectric actuator. As a result, the voltages or other electrical signals include information about the position and/or movement of the piezoelectric actuator and may be used to estimate the position and/or movement of the piezoelectric actuator and/or the cantilevered optical fiber. In one or more embodiments of the invention, the piezoelectric actuator may then be actuated based at least in part on the detected voltages. That is, the detected voltages may serve as a sort of feedback to guide further actuation. As will be explained further below, this information or feedback may be used during active driving, or during braking at the end of a scan.

Figure 7:
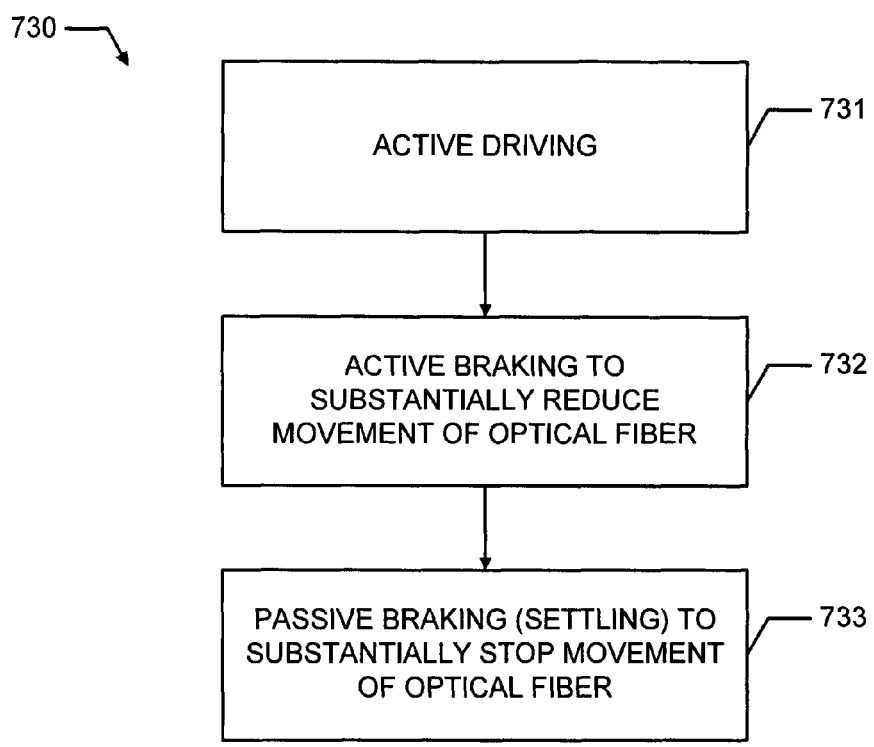
FIG. 7 is a block flow diagram of a method that may be performed during one frame of image construction, according to embodiments of the invention.

FIG. 7 is a block flow diagram of a method 730 that may be performed during one frame of image construction, according to embodiments of the invention.

Initially, active driving may be performed, at block 731. This may be performed substantially as previously discussed. In particular, during the active driving, actuator drive signals may be applied to a piezoelectric actuator in order to cause the piezoelectric actuator to actuate a cantilevered optical fiber according to a scan.

Then, after the scan, active braking may be performed, at block 732. The active braking may involve applying actuator drive signals to the piezoelectric actuator that are operable to cause the piezoelectric actuator to actuate the cantilevered optical fiber in a way that substantially reduces the movement of the cantilevered optical fiber. As used herein, substantially reducing the movement of the cantilevered optical fiber means reducing the movement of the cantilevered optical fiber by at least 50%. By way of example, in the case of a spiral scan, signals similar to the actuator drive signals used during active driving, but about 180° out of phase relative to, and potentially having either greater or lesser amplitude, may be used for active braking. Note actuation may either be used to increase or reduce movement of the cantilevered optical fiber.

Next, after the active braking, passive braking (settling) may be performed, at block 733. The passive braking may involve merely waiting for a period of time to allow the cantilevered optical fiber to settle or substantially stop moving. This may prepare the cantilevered optical fiber for a subsequent frame of image construction. In one aspect, the method may optionally cycle through blocks 731-733 once each frame at a given frame rate.

Active braking is generally able to reduce the movement of the cantilevered optical fiber more rapidly than passive braking. As one illustrative but non-limiting example, about 8 cycles of active braking may be capable of removing about 80% of the movement of the cantilevered optical fiber, whereas it may take around 50 or more cycles of passive braking to remove the remaining 20% of the movement. These numbers may vary from one implementation to another.

Active braking is often desired in order to help to increase the frame rate. However, it tends to be difficult to accurately know the position and/or movement of the piezoelectric actuator and/or cantilevered optical fiber toward the end of active braking. Furthermore, if the position and/or movement differs from what is expected, then the active braking may potentially unintentionally increase the movement of the cantilevered optical fiber, rather than decreasing the movement of the cantilevered optical fiber. As a result, active braking may be stopped prematurely or sooner than would be desirable.

Figure 8:
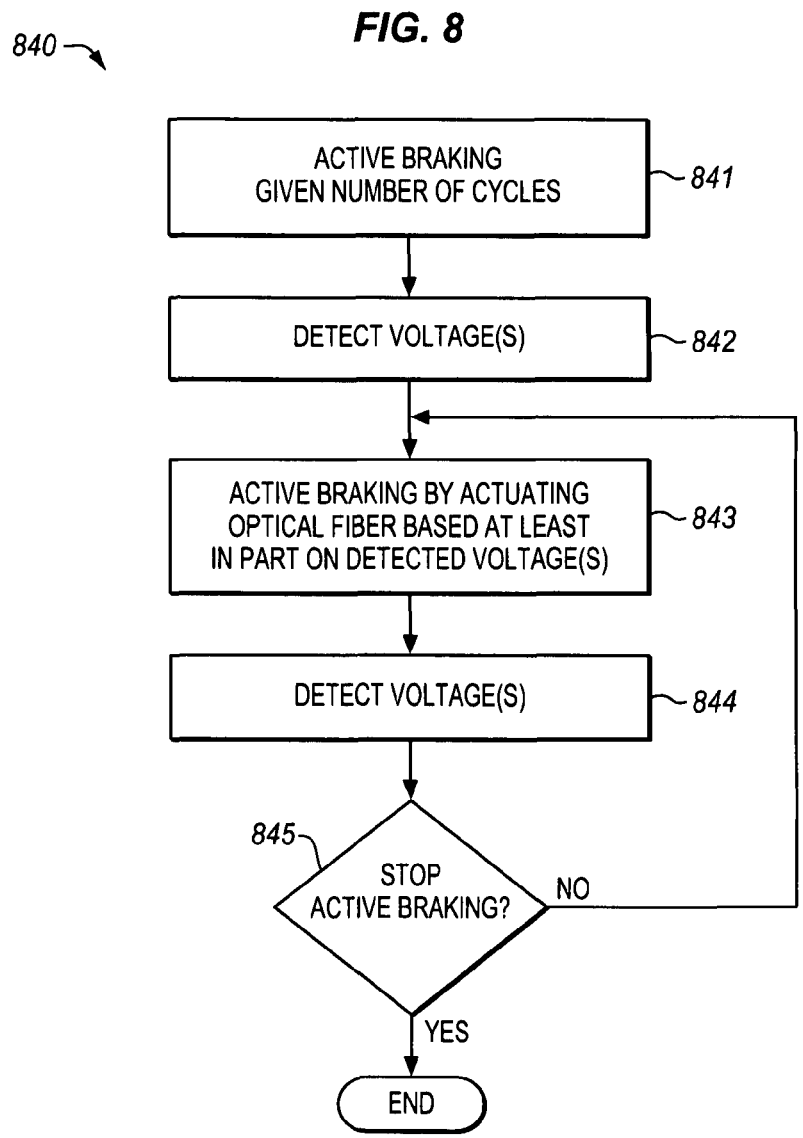
FIG. 8 is a block flow diagram of a method of active braking, according to embodiments of the invention.

In one or more embodiments of the invention, voltages or other electrical signals generated by the piezoelectric actuator may be detected and used during active braking. FIG. 8 is a block flow diagram of a method 840 of active braking, according to embodiments of the invention.

Initially, conventional active braking may optionally be performed for a given number of cycles, at block 841. The given number may be less than a number of cycles at which the movement of the cantilevered optical fiber begins to become un-predictable with further active braking. By way of example, the given number may be such that from about 30 to 80% of the movement of the cantilevered optical fiber is reduced. As another example, the given number of cycles may be a single cycle.

Then, one or more voltages generated by the piezoelectric actuator as a result of mechanical deformation or stress associated with movement may be detected, at block 842. These voltages may be detected as previously described.

Next, active braking by actuating the cantilevered optical fiber based, at least in part, on the one or more detected voltages may be performed, at block 843. That is, the detected voltages may be used as a sort of feedback to adjust the way in which subsequent actuation is performed. In one or more embodiments of the invention, this may include determining an actuator drive signal based, at least in part, on the detected voltage, and applying the determined actuator drive signal to the piezoelectric actuator to achieve active braking.

This may offer a number of potential advantages. For one thing, this may help to improve the active braking of the cantilevered optical fiber. For another thing, this may help to avoid a situation in which the active braking has the unintentionally affect of increasing (rather than reducing) the movement of the cantilevered optical fiber. For yet another thing, this may help to allow active braking to be performed longer than would generally be possible if the voltages were not detected.

Then, one or more voltages generated by the piezoelectric actuator as a result of mechanical deformation or stress associated with movement may again be detected, at block 844. These voltages may be detected as previously described.

Next, a determination may be made whether to stop active braking, at block 845. In one or more embodiments of the invention, this determination may be made based on the one or more detected voltages from block 844. For example, if a voltage detected at block 844 is greater than or equal to a corresponding voltage detected at block 842, or if the detected voltages otherwise seem to indicate that active braking at block 843 resulted in an increase in movement, then it may be determined to stop active braking. Otherwise, it may be determined to continue active braking.

Other ways of making the determination at block 845 are also possible. For example, in one or more embodiments of the invention, a determination may be made whether a count of a number of times active braking at block 843 has been performed this frame is equal to or greater than a given number. If the count is equal to or greater than the given number, then it may be determined to stop active braking. Otherwise, it may be determined to continue active braking. These are just a few illustrative examples.

If "no" is the determination at block 845 (i.e., it is determined not to stop active braking), then the method may revisit block 843. Otherwise, the method may end, at block 846.

A particular method has been shown and described in order to illustrate certain concepts, although the scope of the invention is not limited to this particular method. As one example, voltages may be detected throughout active braking, rather than after performing conventional active braking a given number of cycles. As another example, the determination at block 845 may optionally be omitted in favor of simply repeating the method a predetermined number of times. As yet another example, rather than active braking based on the detected voltages, only conventional active braking may be performed. The detected voltages may instead merely be used to determine when to stop conventional active braking, for example if an increase in motion is detected. Various other modifications of the above-described method and are also contemplated.

Now, voltages may also or alternatively be detected and used during active driving, according to one or more embodiments of the invention. As one example, one or more voltages may be detected at the end of a scan, such as, for example, at the end of a spiral scan. The one or more detected voltages may be used to estimate the maximum diameter of the spiral scan or otherwise estimate the extent or level of focus of the scan. Then, if appropriate, an actuator drive signal to use during a subsequent scan may be determined based, at least in part, on the one or more detected voltages in order to help make the position and/or movement more as expected or intended. For example, actuator drive voltages may be increased to increase the spiral diameter, or decreased to decrease the spiral diameter. As another example, if an elliptical spiral is detected (when a circular spiral is desired), then the voltages on the wider axis may be reduced relative to the voltages on the narrower axis to make the ellipse more circular. Other uses for the detected voltages are also contemplated. For example, the detected voltages may be used to perform image remapping or otherwise adjust images constructed using the scanning fiber system. Still other uses will be apparent to those skilled in the art and having the benefit of the present disclosure.

Figure 9:
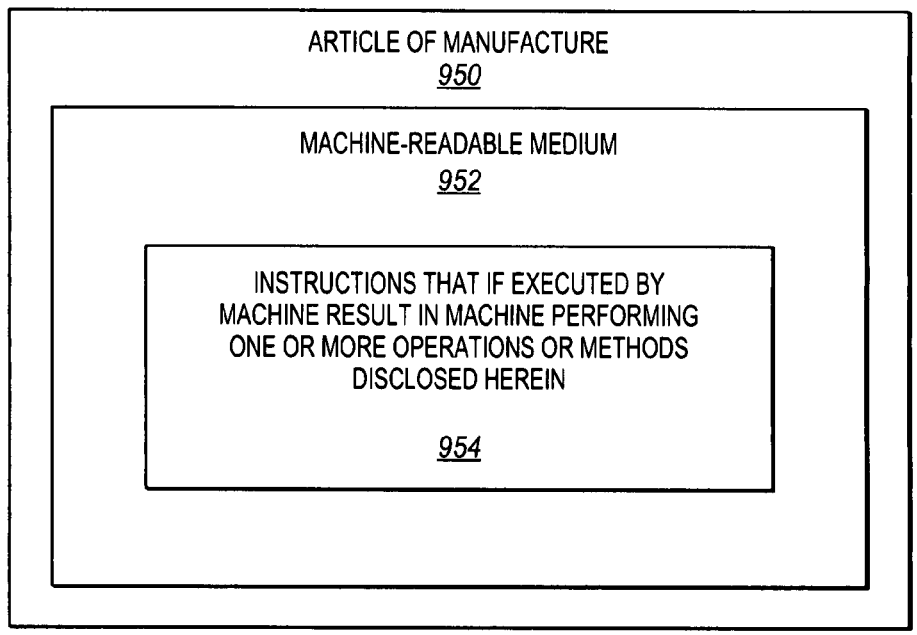
FIG. 9 is a block flow diagram of an article of manufacture, according to embodiments of the invention.

FIG. 9 is a block flow diagram of an article of manufacture 950, according to embodiments of the invention. The article of manufacture includes a machine-readable medium 952. Examples of suitable types of machine-readable mediums include, but are not limited to, floppy diskettes, optical storage mediums, optical disks, CD-ROMs, magnetic disks, magneto-optical disks, read only memories (ROMs), programmable ROMs (PROMs), erasable-and-programmable ROMs (EPROMs), electrically-erasable-and-programmable ROMs (EEPROMs), random access memories (RAMs), static-RAMs (SRAM), dynamic-RAMs (DRAMs), Flash memories, other machine-readable mediums, and combinations thereof.

The machine-readable medium is readable by a machine. Examples of suitable machines include, but are not limited to, base stations, endoscope base stations, scanning fiber systems, scanning fiber image acquisition systems, scanning fiber image display systems, medical equipment, computer systems, and a wide variety of other devices with one or more processors or processing circuits, to name just a few examples.

Stored or otherwise provided in and/or on the machine-readable medium are instructions 954 that if executed by the machine result in the machine performing one or more operations or methods as disclosed herein. For example, the instructions if executed by the machine may result in the machine estimating a position and/or movement of the cantilevered optical fiber and/or the piezoelectric actuator based on one or more detected voltages or other electrical signals. As another example, the instructions if executed by the machine may result in the machine determining an actuation and/or actuator drive signal based at least in part on one or more detected voltages or other electrical signals.

The machine may include a position estimation unit to estimate a position of one or more of the piezoelectric actuator and a cantilevered optical fiber coupled with the piezoelectric actuator based at least in part on the detected voltage. The machine may also include an actuator drive signal determination unit to determine an actuator drive signal based at least in part on the detected voltage. Each of these units is a means that can be implemented using software, hardware or a combination thereof.

In the description above, for the purposes of explanation, numerous specific details have been set forth in order to provide a thorough understanding of the embodiments of the invention. The particular embodiments described are not provided to limit the invention but to illustrate it. Embodiments may be practiced without some of these specific details. Furthermore, modifications may be made to the embodiments disclosed herein, such as, for example, to the configurations, functions, and manner of operation, of the components of the embodiments. All equivalent relationships to those illustrated in the drawings and described in the specification are encompassed within embodiments of the invention. The scope of the invention is not to be determined by the specific examples provided above but by the claims below.

Various operations and methods have been described. The methods have been described in a basic form, but operations may optionally be added to the methods. In some cases, operations may be removed from the methods. In some cases, the operations of the methods may be performed in different order. Many modifications and adaptations may be made to the methods and are possible and contemplated.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A method comprising:
   inhibiting modification of an electric signal generated by a piezoelectric tube by controlling a switch to switchably electrically decouple actuator drive signals from a first line coupled with the piezoelectric tube;
   detecting the electrical signal generated by the piezoelectric tube as a result of mechanical deformation of the piezoelectric tube while the actuator drive signals are switchably electrically decoupled from the piezoelectric tube due to said inhibiting on a second high impedance line having an impedance of at least one mega ohm which is coupled between a voltage detector and the first line, the piezoelectric tube operable to actuate a cantilevered optical fiber inserted though the piezoelectric tube, wherein detecting the electrical signal comprises detecting the electrical signal during a period of active braking;
   determining an active braking actuator drive signal based at least in part on the electrical signal generated by the piezoelectric tube that is detected during the period of the active braking, the active braking actuator drive signal operable to cause the piezoelectric tube to reduce movement of the cantilevered optical and fiber;
   applying the active braking actuator drive signal to the piezoelectric tube;
   detecting a second electrical signal generated by the piezoelectric tube; and
   determining to stop active braking based at least in part on the detected second electrical signal indicating an increase in movement of the piezoelectric tube.

2. The method of claim 1, further comprising estimating a position of at least one of the piezoelectric tube and the cantilevered optical fiber based on the detected electrical signal.

3. The method of claim 1, wherein detecting the electrical signal comprises detecting the electrical signal on a first side of the piezoelectric tube, and further comprising detecting a second electrical signal on a second side of the piezoelectric tube that is orthogonal to the first side.

4. The method of claim 1, further comprising inserting the cantilevered optical fiber into a patient.

5. An apparatus comprising:
   a connector interface to allow a scanning fiber device to be connected;
   a light source optically coupled with the connector interface to provide light to the scanning fiber device through the connector interface;
   an actuator driver to provide actuator drive signals to a piezoelectric actuator of the scanning fiber device through a path through the connector interface; and
   a switch electrically coupled with the actuator driver and with the connector interface and operable to switchably electrically couple or not electrically couple the actuator driver with the connector interface;
   a voltage detector to detect a first voltage and a second voltage both generated due to mechanical deformation of the piezoelectric tube that are returned through the path through the connector interface, wherein the voltage detector is to detect the first and second voltages while the actuator driver is electrically decoupled from the path through the connector interface on a high impedance line which has an impedance of at least one mega ohm and which is coupled between the path and the voltage detector, wherein the voltage detector is to detect the first and second voltages during a period of active braking;
   an actuator drive signal determination unit in communication with the voltage detector and the actuator driver and operable to determine an active braking actuator drive signal based at least in part on the first voltage detected during the period of active braking; and
   a unit to determine to stop active braking based at least in part on the detected second voltage indicating an increase in movement of the piezoelectric actuator.

6. The apparatus of claim 5, wherein the voltage detector is switchably electrically coupled with the connector interface.

7. The apparatus of claim 5, wherein the voltage detector is electrically coupled with the switch, and wherein the switch is operable to switchably electrically couple or not couple the voltage detector with the connector interface.

8. The apparatus of claim 5, wherein the high impedance line comprises a high impedance amplifier.

9. The apparatus of claim 5, wherein the voltage detector is electrically coupled with a plurality of conductive paths, and wherein the plurality of conductive paths are at least switchably electrically coupled with a corresponding plurality of electrodes on orthogonal sides of the piezoelectric actuator.

10. The apparatus of claim 5, further comprising a position estimation unit to estimate a position of one or more of the piezoelectric actuator and a cantilevered optical fiber coupled with the piezoelectric actuator based at least in part on the detected voltage.

11. The method of claim 1, wherein detecting comprises detecting an electrical signal on a wire while an electrical signal for actuation is not applied to the wire.

12. The apparatus of claim 5, wherein the path through the connector interface comprises a second line, and wherein the voltage detector is to detect the voltage on the line when the actuator drive signals are not applied to the second line.

13. A method comprising:
   actuating a cantilevered optical fiber by applying actuator drive signals to a piezoelectric tube, the optical fiber inserted through the piezoelectric tube;

inhibiting modification of an electric signal generated by the piezoelectric tube by electrically decoupling the actuator drive signals from the piezoelectric tube, wherein electrically decoupling the actuator drive signals from the piezoelectric tube comprises controlling a switch to switchably electrically decouple the actuator drive signals from the piezoelectric tube;

detecting the electrical signal generated by the piezoelectric tube when the actuator drive signals are not applied to the piezoelectric tube, wherein detecting the electrical signal generated by the piezoelectric tube is performed during a period of active braking;

applying a braking signal to the piezoelectric tube, in which the braking signal has been determined based upon the electrical signal detected during the period of active braking, and in which the braking signal is operable to reduce movement of the piezoelectric tube;

detecting a second electrical signal generated by the piezoelectric tube when the actuator drive signals are not applied to the piezoelectric tube during the period of active braking; and determining to stop the active braking based at least in part on the detected second electrical signal indicating an increase in movement of the piezoelectric tube.

14. The method of claim 1, wherein the detection of the electrical signal is performed after from 30 to 80% of the movement of the cantilevered optical fiber has been reduced.

15. The method of claim 1, in which applying the active braking actuator drive signal to the piezoelectric tube comprises applying an active braking actuator drive signal that is 180 degrees out of phase relative to an actuator drive signal that was previously used to increase the movement of the cantilevered optical fiber.

16. The apparatus of claim 5, further comprising the scanning fiber device connected to the connector interface, and wherein the piezoelectric actuator comprises a piezoelectric tube through which a cantilevered optical fiber of the scanning fiber device is inserted.

17. The method of claim 13, wherein detecting the electrical signal is after the electrical signal has passed over a high impedance line having an impedance of at least one mega ohm.

* * * * *